United States Patent [19]

Hiyamuta et al.

[11] Patent Number: 6,010,903
[45] Date of Patent: Jan. 4, 2000

[54] ANTI-HUMAN CERULOPLASMIN MONOCLONAL ANTIBODY

[75] Inventors: Shuichi Hiyamuta; Keiko Shimizu; Akihiko Kadota, all of Sodegaura, Japan

[73] Assignee: Idemitsu Kosan Company Limited, Tokyo, Japan

[21] Appl. No.: 08/418,385

[22] Filed: Apr. 7, 1995

Related U.S. Application Data

[63] Continuation of application No. 08/029,582, Mar. 11, 1993, Pat. No. 5,491,066.

[30] Foreign Application Priority Data

Jan. 13, 1993 [JP] Japan ........................... 5-20621

[51] Int. Cl.$^7$ ........................... C12N 5/20; G01N 33/573; C07K 16/40
[52] U.S. Cl. ................ 435/338; 435/7.4; 435/70.21; 435/172.2; 435/337; 435/25; 436/548; 436/811; 530/388.25; 530/388.26; 935/104; 935/110
[58] Field of Search .................. 530/388.26, 388.25; 435/7.4, 25, 240.27, 70.21, 172.2, 337, 338; 436/548, 811; 935/104, 100, 110

[56] References Cited

U.S. PATENT DOCUMENTS

| | | | |
|---|---|---|---|
| 4,780,401 | 10/1988 | Heusser | 435/7.4 |
| 5,491,066 | 2/1996 | Hiyamuta et al. | 435/7.4 |

OTHER PUBLICATIONS

Schosinsky et al., Clin. Chem 20 (12):1556–1563.
36th Japan Human Genetics Society (1991), Abstract.
Biokhymiya (1990) 55:361–367. Megrabian et al. (Monoclonal Antibodies to Ceruloplasmin).
Saenko et al., Abstract 92082901, 56(9):1640–1646 (1991).
Puchkova et al., Biological Abstracts, 90(50705) (1990).
Abstract of JP6268987—"Anti–human Ceruloplasmin Monoclonal Antibody, Used in Diagnosis of Liver Diseases, Wilson's Disease, etc. —...".
Matsuda et al., Ped. Res., 8:821–824 (1974).
Hellstrom et al., "Monoclonal Antibodies for Cancer Detection and Therapy," (RW Baldwin, ed), Academic Press, London, p. 20 (1985).
Shaposhnikov et al., Experientia, 25:424–426.
Hudson et al., Practical Immunology, Blackwell Scientific Publications, Oxford, p. 120 (1980).
Puchkova et al., "An Experiment for the Detection of the Wilson–Konovalov Mutation . . .", Author's Collective, 1989 Zh Nevropatol Psikhiatr IM SS Korsakova 89: 14–18.
Saenko et al, Mar. 1991. Immunoenzyme determination of total serum ceruloplasim Application to Wilson Disease. Biochemisty International 23(5):819–824.

*Primary Examiner*—Christopher L. Chin
*Assistant Examiner*—James L. Grun
*Attorney, Agent, or Firm*—Birch, Stewart, Kolasch & Birch, LLP

[57] ABSTRACT

Disclosed is a monoclonal antibody which specifically reacts with active human ceruloplasmin as well as a method for diagnosing Wilson's disease using the same. The monoclonal antibody of the present invention specifically reacts with active human ceruloplasmin, it neutralizes the peroxidase activity of the active human ceruloplasmin upon binding thereto, and it does not specifically react with inactive human ceruloplasmin.

7 Claims, 7 Drawing Sheets

ANTI-HUMAN CERULOPLASMIN MONOCLONAL ANTIBODY

This application is a continuation of application Ser. No. 08/029,582, filed on Mar. 11, 1993, now U.S. Pat. No. 5,491,066, the entire contents of which are hereby incorporated by reference.

BACKGROUND OF THE INVENTION

I. Field of the Invention

This invention relates to a monoclonal antibody specific to active human ceruloplasmin, a method for detecting or quantifying human ceruloplasmin using the same, and to a method for diagnosing Wilson's disease using the same.

II. Description of the Related Art

Ceruloplasmin is a kind of plasma protein, which is found in the $\alpha_2$ macroglobulin fraction. It is a copper-containing glycoprotein, the level of which in normal human serum is 20–50 mg/dl. Therefore, it plays an important role in the metabolism of copper. The ceruloplasmin level in serum of a patient suffering from Wilson's disease, or an infectious disease, or of a pregnant woman is different from that of a normal human, so that quantification of human ceruloplasmin may be used for the diagnosis of these diseases and pregnancy.

Wilson's disease is caused by a decrease in ceruloplasmin activity and presents brain and liver disorders. Although it used to be believed that this disease is caused by a decrease in the amount of ceruloplasmin per se, recently, it was shown that this disease is caused by inactive ceruloplasmin (i.e., sharp decrease in active ceruloplasmin) (36th Japan Human Genetics Society, October, 1991). Thus, a method for directly or indirectly measuring inactive or active human ceruloplasmin is desired. Wilson's disease is one of the rare diseases which is curable by using a chelating agent if the disease is found when the patient is an infant, so that it is desired to detect this disease when the patient is an infant. However, ceruloplasmin activity is intrinsically low in infancy, so that it is difficult to detect Wilson's disease in infants.

It has been proposed to measure ceruloplasmin by measuring the peroxidase activity of ceruloplasmin (Schosinsky et al., Clin. Chem., 201, 1974). However, since there is no substrate which is specific to ceruloplasmin alone, it is impossible to specifically quantify ceruloplasmin alone by peroxidase activity. Further, since this method has low sensitivity, it is impossible to distinguish a Wilson's disease patient from a normal person when the patient is an infant.

It has also been proposed to measure human ceruloplasmin by using a polyclonal antibody specific to human ceruloplasmin (Nippon Rinsho, Vol. 47, Extra Number, p.758, 1989). However, polyclonal antibody specifically reacts with not only active ceruloplasmin but also with inactive ceruloplasmin; thus, it is difficult to distinguish a Wilson's disease patient from a normal person. A monoclonal antibody specific to human ceruloplasmin has also been reported (Biokhimiya, Vol. 55, No. 2, 361–367 (1990)). However, since this monoclonal antibody also reacts with both active and inactive human ceruloplasmin, this monoclonal antibody also cannot be used for the detection of Wilson's disease.

SUMMARY OF THE INVENTION

Accordingly, an object of the present invention is to provide a monoclonal antibody which specifically reacts with active human ceruloplasmin alone.

Another object of the present invention is to provide a method for detecting or quantifying active human ceruloplasmin.

Still another object of the present invention is to provide a method for diagnosing Wilson's disease with high sensitivity.

That is, the present invention provides a monoclonal antibody which specifically reacts with active human ceruloplasmin, which neutralizes the peroxidase activity of the active human ceruloplasmin upon binding thereto, and which does not specifically react with inactive human ceruloplasmin.

The present invention also provides a method for detecting or quantifying active human ceruloplasmin comprising carrying out an immunoassay utilizing the specific binding reaction between the monoclonal antibody of the present invention with active human ceruloplasmin.

The present invention further provides a method for diagnosing Wilson's disease comprising quantifying active human ceruloplasmin in a human body fluid by an immunoassay utilizing the specific binding reaction between the monoclonal antibody of the present invention with active human ceruloplasmin contained in the body fluid.

By the present invention, a monoclonal antibody which specifically reacts with active human ceruloplasmin but not with inactive human ceruloplasmin was first provided. The monoclonal antibody of the present invention specifically reacts with only the active human ceruloplasmin, so that by an immunoassay utilizing this monoclonal antibody, active human ceruloplasmin alone can be quantified. Therefore, by using the monoclonal antibody of the present invention, Wilson's disease can be detected with high sensitivity. Particularly, as shown in the Examples described below, infant patients suffering from Wilson's disease were detected by the method of the present invention. Thus, the present invention will greatly contribute to the diagnosis of Wilson's disease and other diseases associated with the change in amount of ceruloplasmin.

DETAILED DESCRIPTION OF THE PREFERRED EMBODIMENTS

Figure 1A:
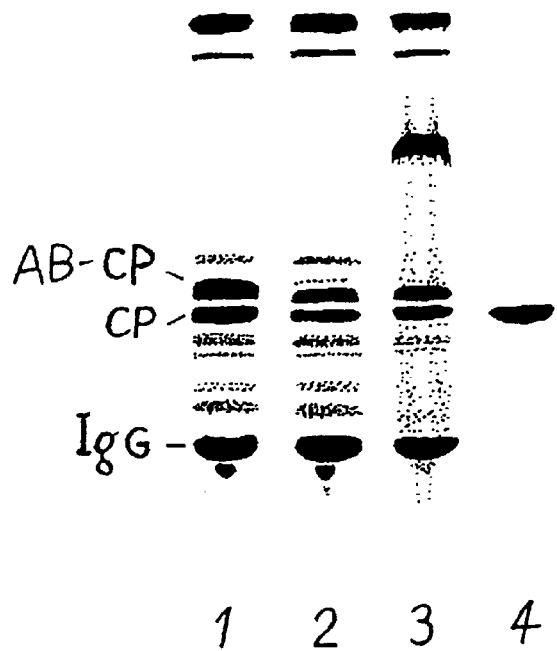
FIGS. 1A and 1B schematically show an electrophoretic pattern indicating the results of examination of the peroxidase activity-neutralizing abilities of monoclonal antibodies.

As mentioned above, the monoclonal antibody of the present invention specifically reacts with active human ceruloplasmin and neutralizes the peroxidase activity of the active human ceruloplasmin upon binding thereto, but does not specifically react with inactive human ceruloplasmin. In the Examples hereinbelow described, a monoclonal antibody CP4 which has the properties just mentioned above was obtained. Hybridoma CP4 producing monoclonal antibody CP4 was deposited with NATIONAL INSTITUTE OF BIOSCIENCE AND HUMAN-TECHNOLOGY (formerly FERMENTATION RESEARCH INSTITUTE) of 1–3, Higashi 1-chome, Tsukuba-shi Ibaraki-ken 305 Japan on Aug. 7, 1991 under the Budapest Treaty under an accession number of FERM BP-4145.

The monoclonal antibody of the present invention may be obtained as follows:

First, a mammal is immunized with active human ceruloplasmin. Purified human ceruloplasmin including active human ceruloplasmin is commercially available from Sigma, Chemicon, Carbiochem, and so on and such a commercially available human ceruloplasmin may be used as the immunogen. The mammal is not restricted and may be a primate, a rodent such as mouse, rat or rabbit, bovine, sheep, goat or dog.

Then antibody-producing cells such as spleen cells are removed from the immunized animal and are fused with myeloma cells. The myeloma cells are well-known in the art and p3x63-Ag8-653, NS-0, NS-1 or P3U1 cells may be used. The cell fusion operation may be carried out by a well-known conventional method.

The cells, after being subjected to the cell fusion operation, are then cultured in HAT selection medium so as to select hybridomas. Hybridomas which produce anti-human monoclonal antibodies are then screened. This screening may be carried out by, for example, sandwich ELISA (enzyme-linked immunosorbent assay) or the like in which the produced monoclonal antibodies are bound to the wells to which human ceruloplasmin is immobilized. In this case, as the secondary antibody, an antibody specific to the immunoglobulin of the immunized animal, which is labelled with an enzyme such as peroxidase, alkaline phosphatase, glucose oxidase, β-D-galactosidase or the like, may be employed. The label may be detected by reacting the labelling enzyme with its substrate and measuring the generated color. As the substrate, 3,3-diaminobenzidine, 2,2-diaminobis-o-dianisidine, 4-chloronaphthol, 4-aminoantipyrine, o-phenylenediamine or the like may be produced.

By the above-described operation, hybridomas which produce anti-human ceruloplasmin antibodies can be selected. The selected hybridomas are then cloned by the conventional limiting dilution method or soft agar method. If desired, the cloned hybridomas may be cultured on a large scale using a serum-containing or a serum free medium, or may be inoculated into the abdominal cavity of mice and recovered from ascites, thereby a large number of the cloned hybridomas may be obtained.

Among the thus selected anti-human ceruloplasmin monoclonal antibodies, those which have an ability to neutralize the peroxidase activity of human ceruloplasmin are then selected. This may be carried out by forming an antigen-antibody complex between the purified human ceruloplasmin including active ceruloplasmin and the monoclonal antibody of interest and then measuring the peroxidase activity of the complex by reacting it with a substrate such as 3-diaminobenzidine. If the antigen-antibody complex does not have peroxidase activity, it means that the monoclonal antibody tested has an ability to neutralize the peroxidase activity of human ceruloplasmin. That is, the monoclonal antibody specifically recognizes the peroxidase active site of active human ceruloplasmin. Finally, the thus selected monoclonal antibody is then tested for its ability to specifically react with inactive human ceruloplasmin. This can be also carried out by the above-mentioned sandwich ELISA or the like. If the monoclonal antibody does not specifically react with inactive human ceruloplasmin, the monoclonal antibody is the desired monoclonal antibody according to the present invention.

By using the above-described monoclonal antibody of the present invention, active human ceruloplasmin in a sample can be detected or quantified. The detection or quantification of the active human ceruloplasmin in a sample can be carried out by an immunoassay utilizing the specific binding reaction between the monoclonal antibody of the present invention and active human ceruloplasmin. Various immunoassays are well-known in the art and any of them can be employed. Examples of the immunoassays include sandwich method employing the monoclonal antibody and another monoclonal antibody as primary and secondary antibodies, respectively, sandwich method employing the monoclonal antibody and a polyclonal antibody as primary and secondary antibodies, staining methods employing gold colloid, agglutination method, latex method and chemical luminescence. Among these, especially preferred is sandwich ELISA. As is well-known, in this method, a primary antibody is immobilized on, for example, the inner wall of a well and then a sample is reacted with the immobilized primary antibody. After washing, a secondary antibody is reacted with the antigen-antibody complex immobilized in the well. After washing, the immobilized secondary antibody is quantified. As the primary antibody, an antibody which specifically reacts with both active and inactive human ceruloplasmins, especially monoclonal antibody CP3 which was prepared in the Examples hereinbelow described, may preferably be employed. As the secondary antibody, monoclonal antibody CP4 mentioned above may preferably be employed. Alternatively, the primary antibody may be monoclonal antibody CP4 and the secondary antibody may be monoclonal antibody CP3. The quantification of the secondary antibody may be carried out by reacting a labelled antibody (e.g., enzyme-labelled antibody) specific to the immunoglobulin of the animal from which the secondary antibody was obtained with the secondary antibody, and then measuring the label. Alternatively, a labelled (e.g., enzyme-labelled) antibody is used as the secondary antibody and the quantification of the secondary antibody may be carried out by measuring the label on the secondary antibody.

According to the above-described method for quantifying active human ceruloplasmin in a sample, diagnosis of Wilson's disease can be performed by quantifying active human ceruloplasmin in a body fluid such as serum. By this method, even if the ceruloplasmin level is 5 mg/dl or less, as in the case of an infant, the diagnosis of Wilson's disease can be performed.

The invention will now be described by way of examples thereof. It should be noted that the examples are presented for illustration purposes only and should not be interpreted in any restrictive way.

EXAMPLE 1

Preparation of Monoclonal Antibody Specific to Active Human Ceruloplasmin (1) Immunization of Mice Human ceruloplasmin including active ceruloplasmin (commercially available from Sigma) was mixed with an equivolume of Freund's complete adjuvant to form an emulsion. This emulsion was intraperitoneally administered to a mouse (BALB/c, female, 8 weeks old). Two weeks later, additional immunization was carried out with an emulsion of an equivolume mixture of human ceruloplasmin and Freund's incomplete adjuvant. Three or four days before the cell fusion described below, the antigen alone was administered to the mouse through its eyegrounds.

(2) Cell Fusion

Three to four days after the final immunization, spleen was taken out from the mouse immunized in (1). The spleen was disrupted by using a mesh and spleen cells were suspended in PBS. The spleen cells were mixed with myeloma cells (p3x63-Ag8-653) at a ratio of 10:1 and the resulting mixture was left to stand for 3 minutes in the presence of 50% polyethylene glycol. The resulting mixture was centrifuged at 1200 rpm for 8 minutes and the supernatant was removed. The cells were then suspended in HAT RPMI-1640 medium containing 10% FCS at a population density of $3.5 \times 10^6$ cells/ml, and the resulting suspension was divided into wells of a 96-well microtiter plate in an amount of 0.1 ml/well. The 96-well microtiter plate was incubated at 37° C. under an atmosphere of 5% $CO_2$. After 2–3 days from the beginning of the incubation, 0.1 ml of HAT RPMI-1640 medium containing 10% FCS was added to each well and then half of the medium was replaced every 3–4 days. After 7–10 days from the beginning of the incubation, colony formation was observed, and sufficient amount of antibody specific to the immunogen was produced in at least one well. The culture supernatants of the antibody-producing wells were then subjected to screening.

(3) Screening

The screening of the antibodies was carried out by ELISA (Immunochemistry, 8:871–874, 1971). That is, to the wells of a 96-well microtiter plate to which 50 µl of an antigen solution in PBS was preliminarily adsorbed, 50 µl of the culture supernatant was placed in each well, and the microtiter plate was incubated at 30° C. for 2 hours. A solution of peroxidase-labelled anti-mouse immunoglobulin antibody was placed in each well and the microtiter plate was incubated at 30° C. for 1 hour. Finally, o-phenylenediamine was added as a substrate. The presence or absence of the anti-human ceruloplasmin antibody was evaluated by the generated color.

(4) Cloning

Cells were taken out from the antigen-specific antibody producing wells and subjected to cloning by the soft agar method. That is, a suspension of hybridomas ($10 \times 10^6$ cells/ml) in HT-RPMI 1640 medium containing 10% FCS was mixed with soft agar and the mixture was divided into petri dishes in an amount of 5 ml/dish. After incubation at 37° C. for 7–10 days, colonies were picked up and the positive colonies were evaluated to be hybridomas producing anti-human ceruloplasmin monoclonal antibody. The above-described cloning procedure was repeated twice to obtain 3 hybridomas producing anti-human ceruloplasmin monoclonal antibody.

(5) Preparation of Monoclonal Antibodies

The hybridomas were transplanted to abdominal cavities of pristane-treated-Balb/c mice. Two to three weeks later, ascites fluids were recovered from the mice.

(6) Activity-neutralizing Ability

Figure 1B:
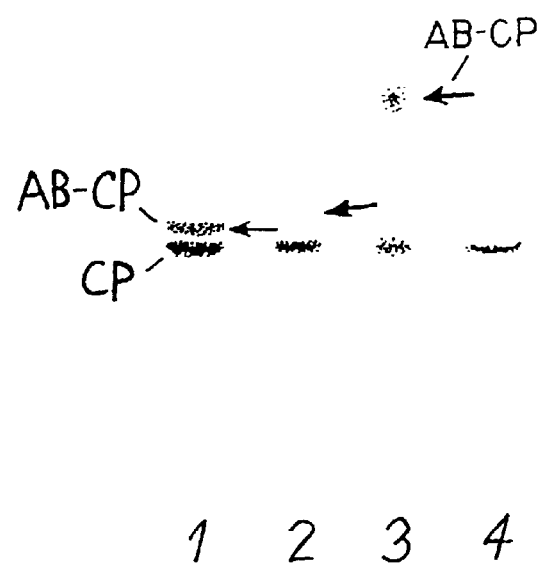

Purified human ceruloplasmin and each ascites containing an antibody obtained in (5) were mixed and the mixture was subjected to 8–25% gradient PAGE after incubation. Thereafter, the peroxidase activities of the formed antigen-antibody complexes were measured. In more detail, this procedure was carried out as follows. That is, 2 µg/ml of purified human ceruloplasmin and each of the three types of the ascites, each containing an antibody (CP3, CP4 or CP13), or PBS were mixed at a ratio of 1:1 (v/v), and the resulting mixtures were incubated at 37° C. for 30 minutes. Thereafter, each of them was subjected to 8–25% gradient native PAGE. The results are shown in FIGS. 1A and 1B. FIG. 1A shows the results obtained by staining with Coomassie Blue and FIG. 1B shows the results obtained by staining utilizing the peroxidase activity. In FIGS. 1A and 1B, AB-CP indicates the complex of purified human ceruloplasmin and the monoclonal antibody and CP indicates purified human ceruloplasmin. In A and B, lane 1, lane 2, lane 3 and lane 4 shows the results of CP3, CP4, CP13 and PBS, respectively. As shown in FIG. 1A, AB-CP is observed in any of lanes 1, 2 and 3. However, in FIG. 1B, the band of AB-CP is observed only in lanes 1 and 3, and no AB-CP band is observed in lane 2. This indicates that the antigen-antibody complexes in lanes 1 and 3 have ceruloplasmin activity while that in lane 2 does not have ceruloplasmin activity. In other words, it was shown that monoclonal antibody CP4 has a ceruloplasmin activity-neutralizing ability. The hybridomas producing CP4 and CP3, respectively, were deposited with NATIONAL INSTITUTE OF BIOSCIENCE AND HUMAN-TECHNOLOGY (formerly FERMENTATION RESEARCH INSTITUTE) of 1–3, Higashi 1-chome, Tsukuba-shi Ibarakiken 305 Japan on Aug. 7, 1991 and on Dec. 25, 1992, under the Budapest Treaty under an accession number of FERM BP-4145 and FERM BP-4133, respectively.

(7) Determination of Molecular Weight of Antigen Fragment

Purified human ceruloplasmin (active human ceruloplasmin) was subjected to 8% SDS gel electrophoresis and immunoblotting was carried out according to a conventional method to determine the molecular weight of the antigen fragment. As a result, it was shown that monoclonal antibody CP4 recognizes a molecule with a molecular weight of 31 kd.

(8) Reactivity with Inactive Human Ceruloplasmin

Active human ceruloplasmin was heated at 100° C. for 3 minutes to obtain an inactive human ceruloplasmin. The reactivities of the thus obtained inactive human ceruloplasmin with CP4 and CP3 were examined. As a result, monoclonal antibody CP3 reacted with the inactive human ceruloplasmin but monoclonal antibody CP4 did not react therewith.

EXAMPLE 2

Figure 2A:
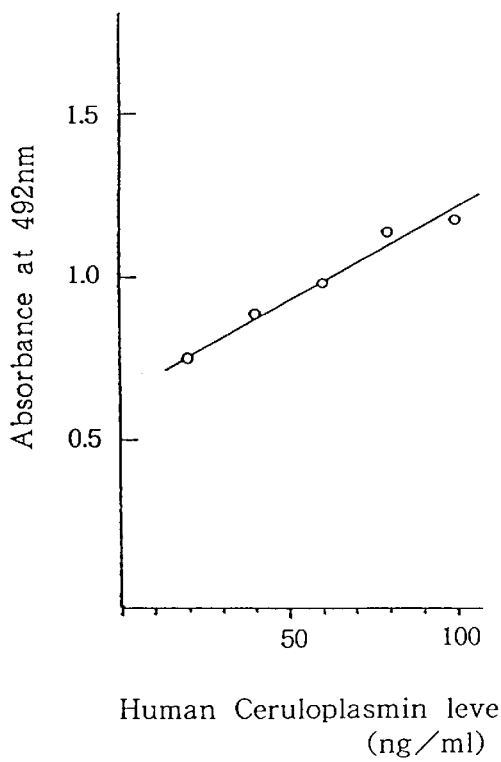
FIGS. 2A and 2B show a calibration curve obtained by measuring known amounts of human ceruloplasmin using monoclonal antibody CP4 according to the present invention.
Figure 2B:
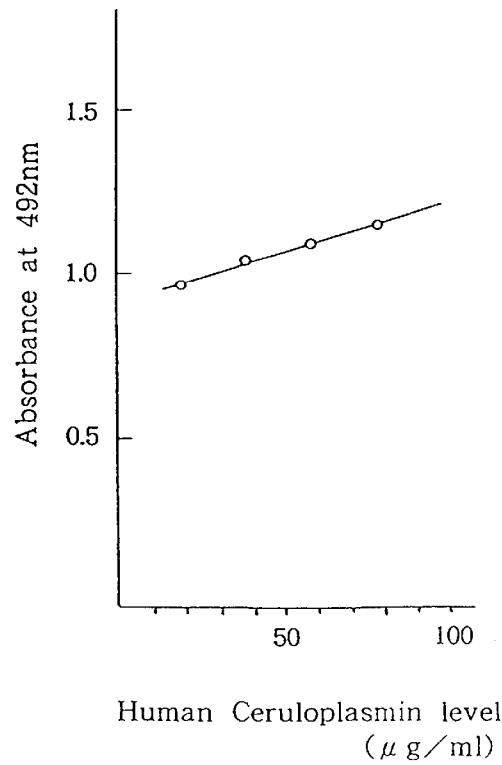

Quantification of Active Human Ceruloplasmin by Sandwich ELISA (1) Preparation of Calibration Curve To each of the wells of a 96-well flat-bottomed microtiter plate, 100 µl of anti-human ceruloplasmin polyclonal antibody was placed and the microtiter plate was left to stand at 4° C. overnight to immobilize the antibody in the wells. After washing the wells with PBS containing Tween 20 three times, 300 µl of a blocking agent was added to each well, and the resultant was left to stand at 30° C. for 2 hours, followed by discarding of the blocking agent. To each of the wells, 100 μl of a human ceruloplasmin solution diluted to 0–100 ng/ml or 0–100 μg/ml was placed and the resultant was incubated at 30° C. for 2 hours. After washing the wells three times, 100 μl of monoclonal antibody CP4 solution was added to each well and the resultant was incubated at 30° C. for 2 hours. The wells were washed three times and 100 μl of peroxidase-labelled anti-mouse IgG antibody (commercially available from Cappel) was added to each well. After incubation at 30° C. for 2 hours, the wells were washed three times and o-phenylenediamine solution was added to each well thereby causing a reaction and the reaction was stopped with 2M $H_2SO_4$. Absorbances of the wells at 492 nm were measured using a plate reader. As a result, the absorbance was increased with the increase in the human ceruloplasmin level, so that calibration curves shown in FIGS. 2A and 2B were obtained. By this, it was proved that human ceruloplasmin can be quantified by using the monoclonal antibody of the present invention.

(2) Quantification of Active Human Ceruloplasmin in Normal Serum

Sera were collected from 4 normal persons and 10,000-fold diluted with PBS. These samples were subjected to the measurement as described in (1). From the calibration curve, the active human ceruloplasmin levels in sera were determined, which were 20–30 mg/dl.

EXAMPLE 3

Quantification of Active Ceruloplasmin by ELISA (Polyclonal Antibody-Monoclonal Antibody Sandwich Method)

Anti-human ceruloplasmin polyclonal antibody (commercially available from Chemicon) as the primary antibody was immobilized on the wells of a 96-well microtiter plate. The immobilization was carried out by placing 100 μl of an antibody solution with a concentration of 10 μg/ml in each well and incubating the resultant at 30° C. for 2 hours or at 4° C. overnight. Then the wells were washed three times with PBS containing 0.05% TWEEN 20. Blocking was then carried out by placing 100 μl of 1–3% BSA solution in each well and incubating the resultant at 30° C. for 2 hours or at 4° C. overnight. After washing the wells in the same manner as described above, 100 μl each of samples being 1000-fold and 10,000-fold dilutions of sera from normal persons and patients suffering from Wilson's disease, were placed in each well and the resulting plate was incubated at 30° C. for 1.5 hours. Further, to prepare a calibration curve, 100 μl of a standard human ceruloplasmin solution (0, 10, 20, 30, 40 or 50 ng/ml) was added to each well, and the plate was incubated in the same manner as described above. After washing the wells in the same manner as described above, 100 μl of peroxidase-labelled CP3 solution or peroxidase-labelled CP4 solution with an antibody level of 10 μg/ml as the secondary antibody was added to each well, and the resultant was incubated at 30° C. for 1.5 hours. After washing the wells in the same manner as described above, 100 μl of a reaction substrate containing 10 mg of o-phenylenediamine and 5 μl of hydrogen peroxide in 25 ml of citrate phosphate buffer was added to each well and the reaction was allowed to occur at 30° C. for 3 minutes. Then 20 μl of 2 M sulfuric acid was added to each well to stop the reaction and the absorbance of each well was measured at 492 nm.

Figure 3:
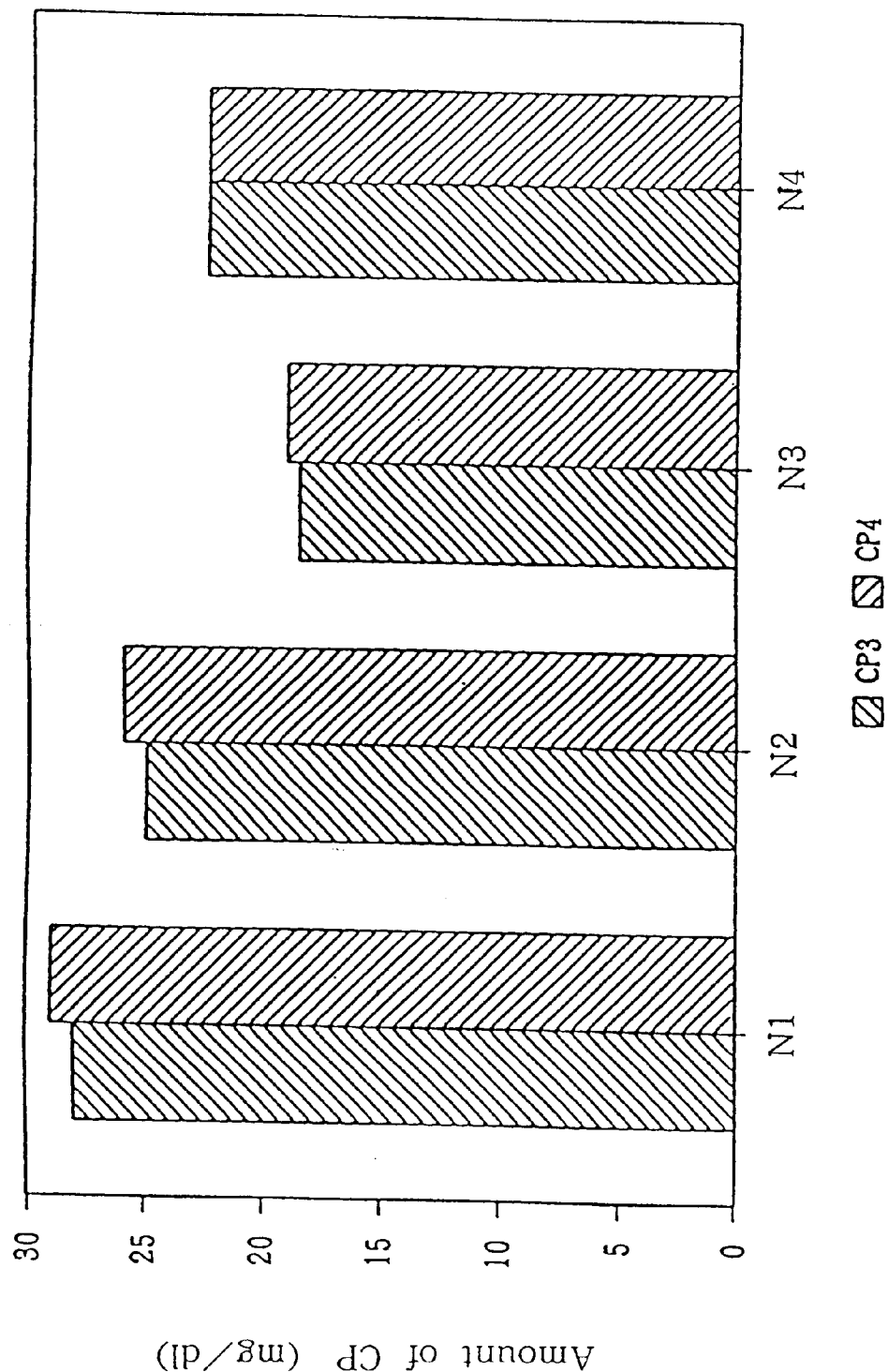
FIG. 3 graphically shows a comparison between the ceruloplasmin protein levels and the active ceruloplasmin levels in a normal human determined by sandwich ELISA according to an example of the present invention.
Figure 4:
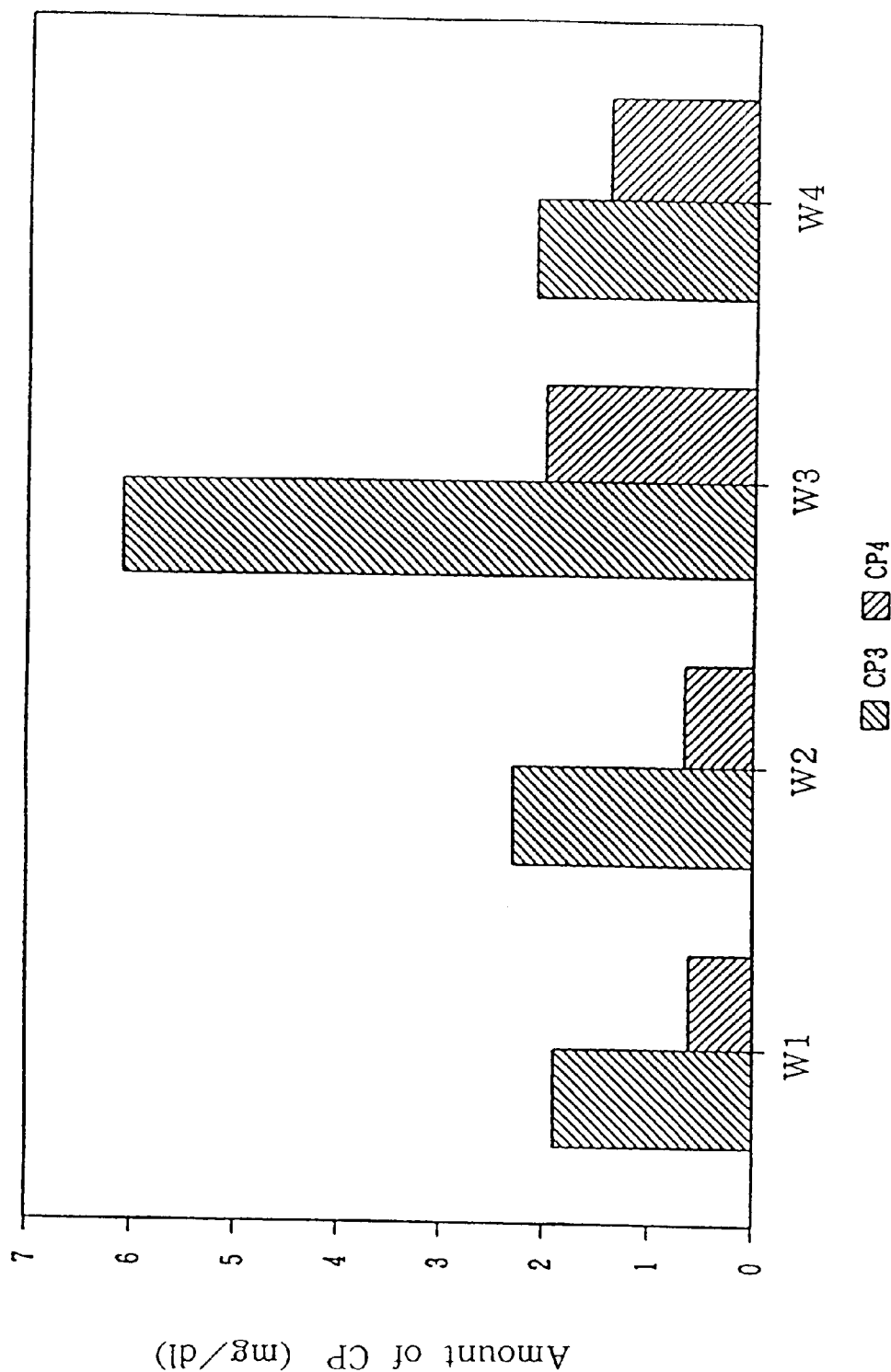
FIG. 4 graphically shows a comparison between the ceruloplasmin protein levels and the active ceruloplasmin levels in patients suffering from Wilson's disease determined by sandwich ELISA according to an example of the present invention.

The results obtained for the normal persons are shown in FIG. 3 and the results obtained for the Wilson's disease patients are shown in FIG. 4. As can be seen from FIG. 3, substantial differences were not observed in the ceruloplasmin levels in the sera of the normal persons when the ceruloplasmin levels were measured using monoclonal antibody CP3 or monoclonal antibody CP4, so that it was shown that inactive ceruloplasmin is not a substantial portion of total ceruloplasmin in a normal human. On the other hand, as for Wilson's disease patients, as can be seen from FIG. 4, since ceruloplasmin levels measured using CP3 are significantly larger than those measured using CP4, a substantial part of the ceruloplasmin is inactive ceruloplasmin. Based on such a difference shown in FIGS. 3 and 4, Wilson's disease can be diagnosed.

EXAMPLE 4

Quantification of Active Ceruloplasmin by ELISA (Monoclonal Antibody-Monoclonal Antibody Sandwich Method)

The same procedure as in Example 3 was repeated except that monoclonal antibody CP3 was used as the primary antibody and monoclonal antibody CP4 was used as the secondary antibody. The measurements were repeated twice on different days. The results are shown in FIG. 5.

Figure 5:
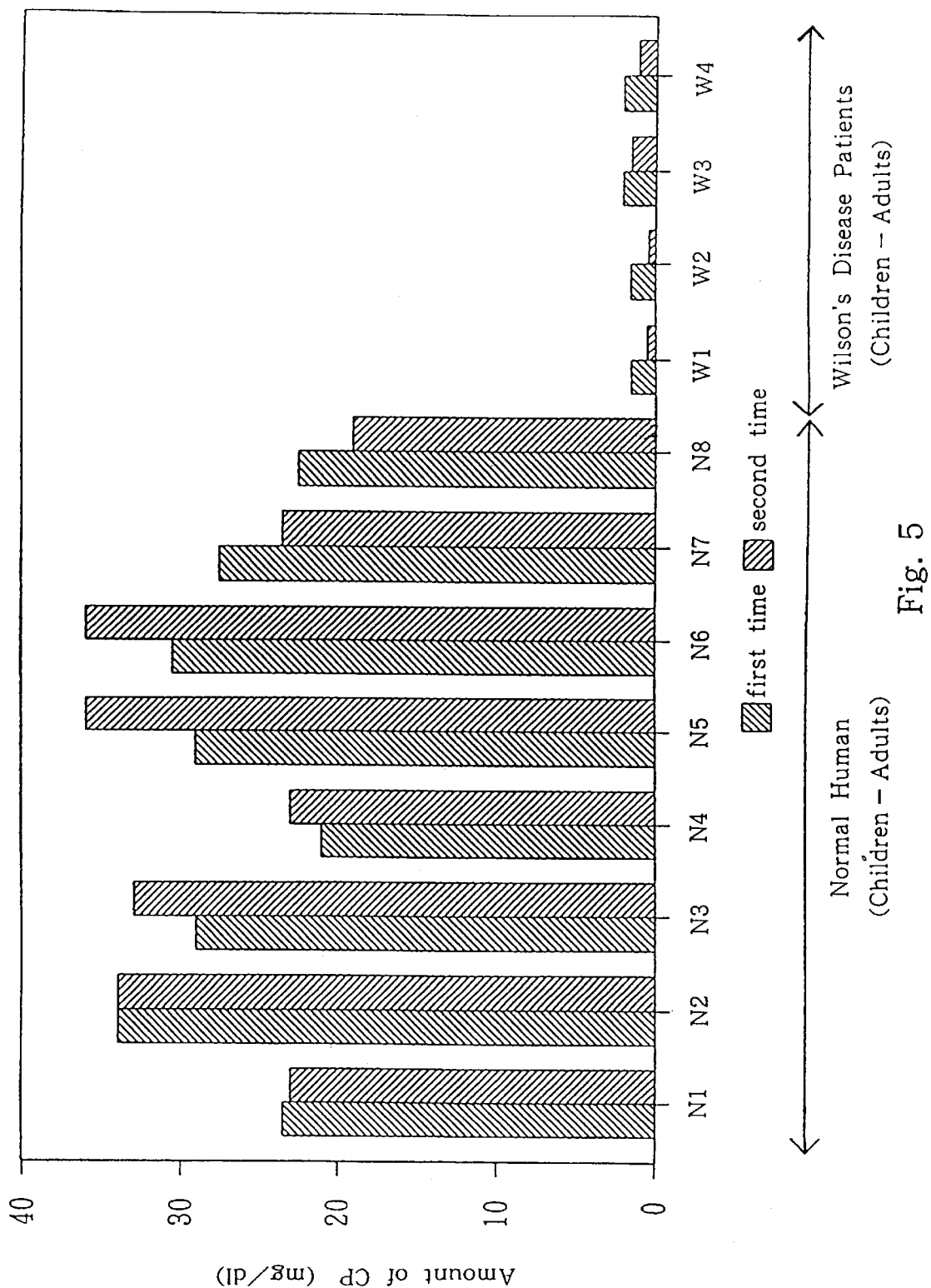
FIG. 5 graphically shows the active ceruloplasmin levels in sera of normal humans and of patients suffering from Wilson's disease, which were determined by sandwich ELISA according to an example of the present invention.

As shown in FIG. 5, although active ceruloplasmin is contained in the blood of normal persons in an amount of 20–40 mg/dl, in the blood of Wilson's disease patients, active ceruloplasmin is contained in an amount of only 0–2 mg/dl.

EXAMPLE 5

In the same manner as in Example 3, active ceruloplasmin levels in sera of normal newborns and of children suffering from Wilson's disease were determined. The results are shown in FIG. 6.

Figure 6:
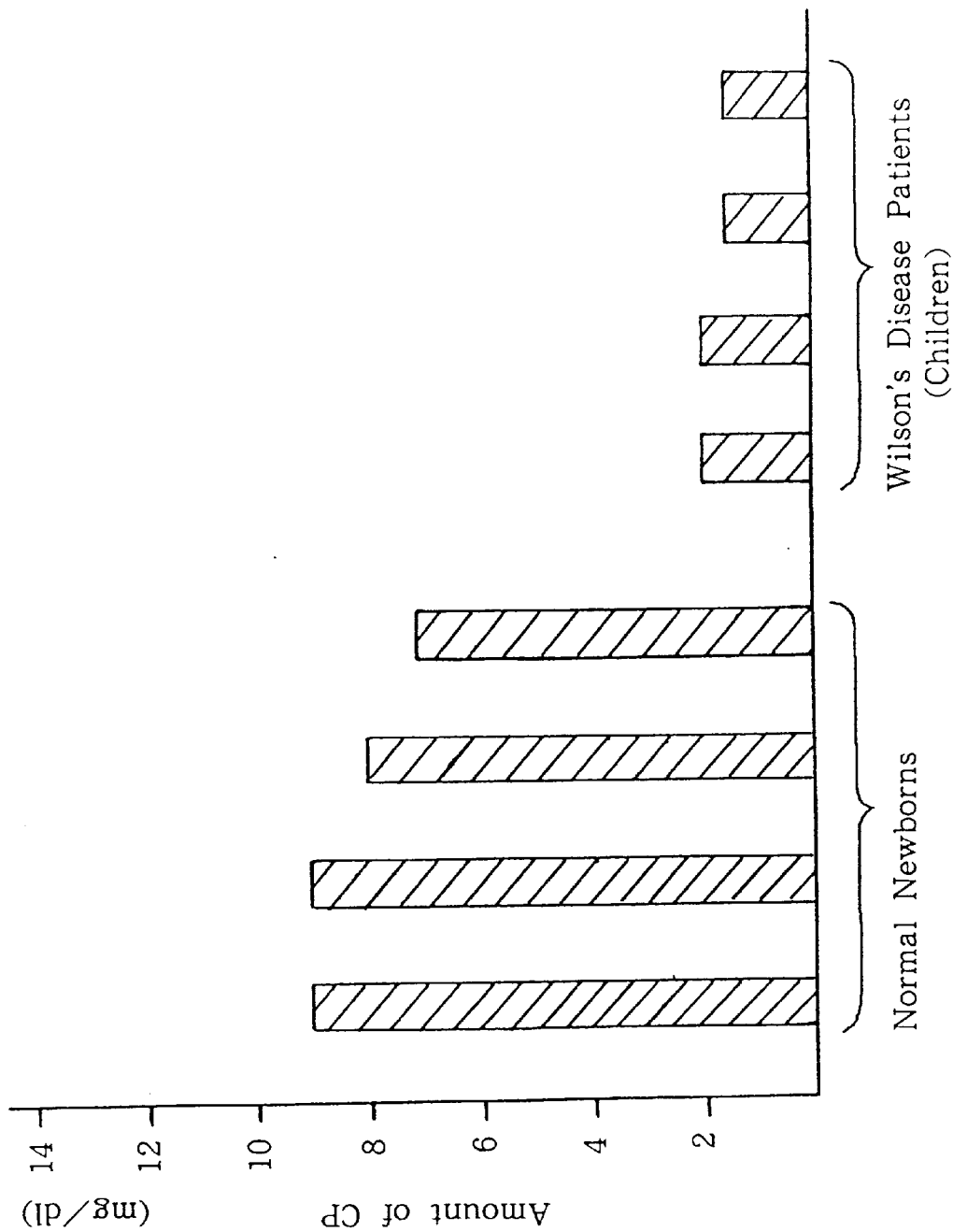
FIG. 6 graphically shows the active ceruloplasmin levels in sera of normal newborns and of children suffering from Wilson's disease, which were determined by sandwich ELISA according to an example of the present invention.

As shown in FIG. 6, a large difference was observed between normal newborns and children suffering from Wilson's disease. It is known that active human ceruloplasmin does not decrease with growth of humans (O. Epstein et al., THE LANCET, Feb. 7, 1981, p303). Therefore, it was proved that Wilson's disease can be definitely diagnosed by the method of the present invention.

COMPARATIVE EXAMPLE 1

Using a conventional polyclonal antibody, ceruloplasmin levels of normal newborns and of children suffering from Wilson's disease were measured by the conventional RIA method. The results are shown in FIG. 7.

Figure 7:
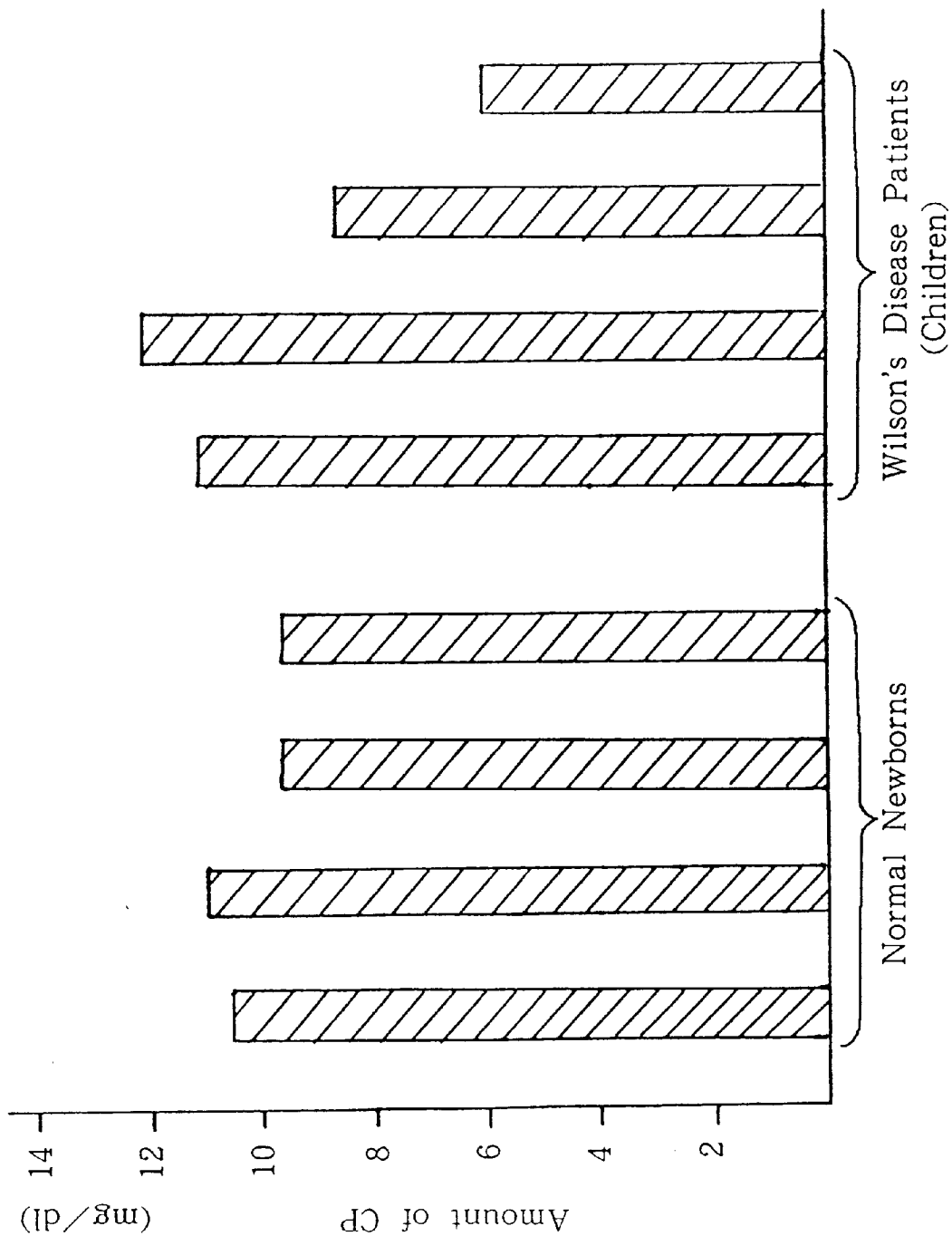
FIG. 7 graphically shows the active ceruloplasmin levels in sera of normal newborns and of children suffering from Wilson's disease, which were determined by a conventional method using a conventional polyclonal antibody.

As shown in FIG. 7, significant differences were not observed between normal newborns and children suffering from Wilson's disease. This is because that by this conventional method, total ceruloplasmin rather than active ceruloplasmin is measured.

We claim:

1. A monoclonal antibody which specifically binds to active human ceruloplasmin, which neutralizes the peroxidase activity of the active human ceruloplasmin upon binding there to, and which does not specifically bind to inactive human ceruloplasmin, wherein said inactive human ceruloplasmin is human ceruloplasmin that has been heat-treated at 100° C. or is inactive human ceruloplasmin in human serum.

2. The monoclonal antibody of claim 1, wherein said inactive human ceruloplasmin is human ceruloplasmin which has been heat-treated at 100° C.

3. A hybridoma which secretes a monoclonal antibody wherein said antibody specifically binds to active human ceruloplasmin, wherein said antibody neutralizes the peroxidase activity of the human ceruloplasmin upon binding thereto, and wherein said antibody further does not bind specifically to inactive human ceruloplasmin, wherein said inactive human ceruloplasmin is human ceruloplasmin that has been heat-treated at 100° C. or is inactive human ceruloplasmin in human serum.

4. A cell line which comprises cells having all identifying properties and characteristics of deposited cell line FERM BP-4145.

5. The cell line of claim 4, which is the cell line deposited as FERM BP-4145.

6. An antibody which has all identifying characteristics of an antibody secreted by deposited hybridoma cell line FERM BP-4145.

7. An antibody secreted by deposited hybridoma FERM BP-4145.

* * * * *